United States Patent
Lietzau

(10) Patent No.: US 9,724,173 B2
(45) Date of Patent: Aug. 8, 2017

(54) USE OF BONE ADHESIVE FOR APICAL SEALING A TOOTH ROOT CANAL

(71) Applicant: Markus Lietzau, Berlin (DE)

(72) Inventor: Markus Lietzau, Berlin (DE)

(*) Notice: Subject to any disclaimer, the term of this patent is extended or adjusted under 35 U.S.C. 154(b) by 0 days.

(21) Appl. No.: 14/043,976

(22) Filed: Oct. 2, 2013

(65) Prior Publication Data
US 2014/0030672 A1    Jan. 30, 2014

Related U.S. Application Data

(62) Division of application No. 12/094,845, filed as application No. PCT/EP2006/011519 on Nov. 24, 2006, now abandoned.

(60) Provisional application No. 60/739,738, filed on Nov. 25, 2005.

(30) Foreign Application Priority Data

Nov. 25, 2005  (EP) ..................................... 05090327
Mar. 17, 2006  (DE) ........................ 10 2006 012 777

(51) Int. Cl.
| | |
|---|---|
| A61C 5/04 | (2006.01) |
| A61C 5/02 | (2006.01) |
| A61K 6/033 | (2006.01) |
| A61K 6/06 | (2006.01) |
| A61C 5/40 | (2017.01) |
| A61C 5/50 | (2017.01) |

(52) U.S. Cl.
CPC .................. *A61C 5/02* (2013.01); *A61C 5/40* (2017.02); *A61C 5/50* (2017.02); *A61K 6/033* (2013.01); *A61K 6/0643* (2013.01)

(58) Field of Classification Search
CPC .. A61C 5/00; A61C 5/04; A61C 5/125; A61K 6/0023; A61K 6/083
USPC ............. 433/80, 81, 89, 90, 224, 226, 228.1
See application file for complete search history.

(56) References Cited

U.S. PATENT DOCUMENTS

| | | | |
|---|---|---|---|
| 73,402 A | 1/1868 | Somborger et al. | |
| 860,555 A | 7/1907 | Middaugh | |
| 1,523,068 A | 1/1925 | Hein | |
| 2,142,780 A | 1/1936 | Fortney | |
| 2,436,623 A * | 2/1948 | Van Zile ............ | A61C 17/0208 134/166 R |
| 3,035,351 A * | 5/1962 | Hirsch ..................... | A61C 5/02 433/224 |

(Continued)

FOREIGN PATENT DOCUMENTS

| | | |
|---|---|---|
| EP | 0 555 807 B1 | 8/1996 |
| WO | 00/33793 A1 | 6/2000 |
| WO | 2005/016368 A2 | 2/2005 |

OTHER PUBLICATIONS

Chohayeb et al., "Evaluation of Calcium Phosphate as a Root Canal Sealer-Filler Material", Journal of Endodontics, vol. 13, No. 8, Aug. 1987, pp. 384-387.*

(Continued)

*Primary Examiner* — Cris L Rodriguez
*Assistant Examiner* — Matthew Saunders
(74) *Attorney, Agent, or Firm* — Ewers & Hasselmann PLLC

(57) ABSTRACT

A method and kit for the apical sealing an tooth root canal and for improving root canal fillings are described. Also described is a method for using bone glue as an apical stop for obturating root canals.

19 Claims, 1 Drawing Sheet

(56) References Cited

U.S. PATENT DOCUMENTS

| | | | | |
|---|---|---|---|---|
| 3,742,955 | A * | 7/1973 | Battista | A61L 15/325 106/157.3 |
| 3,968,567 | A * | 7/1976 | Nevins | A61C 5/04 106/151.1 |
| 4,031,890 | A | 6/1977 | Homan | |
| 4,109,653 | A | 8/1978 | Kozam et al. | |
| 4,184,490 | A | 1/1980 | Jacklich | |
| 4,381,778 | A | 5/1983 | Kozam et al. | |
| 4,526,544 | A * | 7/1985 | Kahn | A61C 5/04 433/224 |
| 4,813,871 | A * | 3/1989 | Friedman | B05C 17/00593 222/386 |
| 4,973,248 | A | 11/1990 | Sigler | |
| 5,141,561 | A * | 8/1992 | Ledard et al. | 106/35 |
| 5,149,368 | A * | 9/1992 | Liu et al. | 424/602 |
| 5,205,833 | A * | 4/1993 | Harsh | A61M 5/344 604/240 |
| 5,415,547 | A * | 5/1995 | Torabinejad | A61C 5/00 433/224 |
| 5,478,321 | A | 12/1995 | Kimber | |
| 5,531,691 | A | 7/1996 | Shonfeld et al. | |
| 5,624,260 | A * | 4/1997 | Wilcox | A61C 5/064 433/90 |
| 5,637,101 | A | 6/1997 | Shillington | |
| 5,695,339 | A | 12/1997 | Abere | |
| 6,059,572 | A * | 5/2000 | Riitano | A61C 5/023 433/224 |
| 6,079,979 | A | 6/2000 | Riitano | |
| 6,162,202 | A * | 12/2000 | Sicurelli | A61C 5/02 604/264 |
| 6,573,312 | B2 * | 6/2003 | Han | A61K 6/0017 522/100 |
| 6,638,064 | B1 | 10/2003 | Nance | |
| 6,811,400 | B2 | 11/2004 | Jensen et al. | |
| 6,972,005 | B2 * | 12/2005 | Boehm, Jr. | A61B 17/00491 222/135 |
| 7,125,254 | B2 * | 10/2006 | Calvert | 433/224 |
| 2002/0146662 | A1 * | 10/2002 | Radl | A61C 5/062 433/90 |
| 2003/0031978 | A1 * | 2/2003 | Garman | A61C 5/04 433/89 |
| 2003/0036762 | A1 | 2/2003 | Fulmer et al. | |
| 2003/0040706 | A1 | 2/2003 | Cohen et al. | |
| 2003/0124482 | A1 * | 7/2003 | Calvert | 433/81 |
| 2005/0066854 | A1 | 3/2005 | Jia | |
| 2005/0069836 | A1 * | 3/2005 | Jia et al. | 433/81 |
| 2005/0282117 | A1 * | 12/2005 | Aravena et al. | 433/224 |
| 2009/0148486 | A1 * | 6/2009 | Lu | A61K 9/0063 424/422 |

OTHER PUBLICATIONS

Hong et al., "The periapical tissue reaction to a calcium phosphate cement in teeth of monkeys", Journal of Biomedical Materials Research, 1991, vol. 25, pp. 485-498.*

Sugawara et al., "Histopathological Reaction of a Calcium Phosphate Cement Root Canal Filler", Journal of Hard Tissue Biology, 1995, 4(1), pp. 1-7.*

Schilder, Herbert, D.D.S., Filling Root Canals in Three Dimensions, The Dental Clinics of North America, Symposium on Endodontics, Nov. 1967.*

Schilder, Herbet. The Dental Clinics of North America; Symposium on Endodontics; Filling Root Canals in Three Dimensions; 1967.*

Chohayeb et al, Evaluation of Calcium Phosphate as a Root Canal Sealer-Filler Material, Journal of Endodontics, vol. 13, Issue 8, Aug. 1987, pp. 384-387.*

Bone Substitutes to Replace Transplantation—Baxter—Oct. 26, 2006.*

* cited by examiner

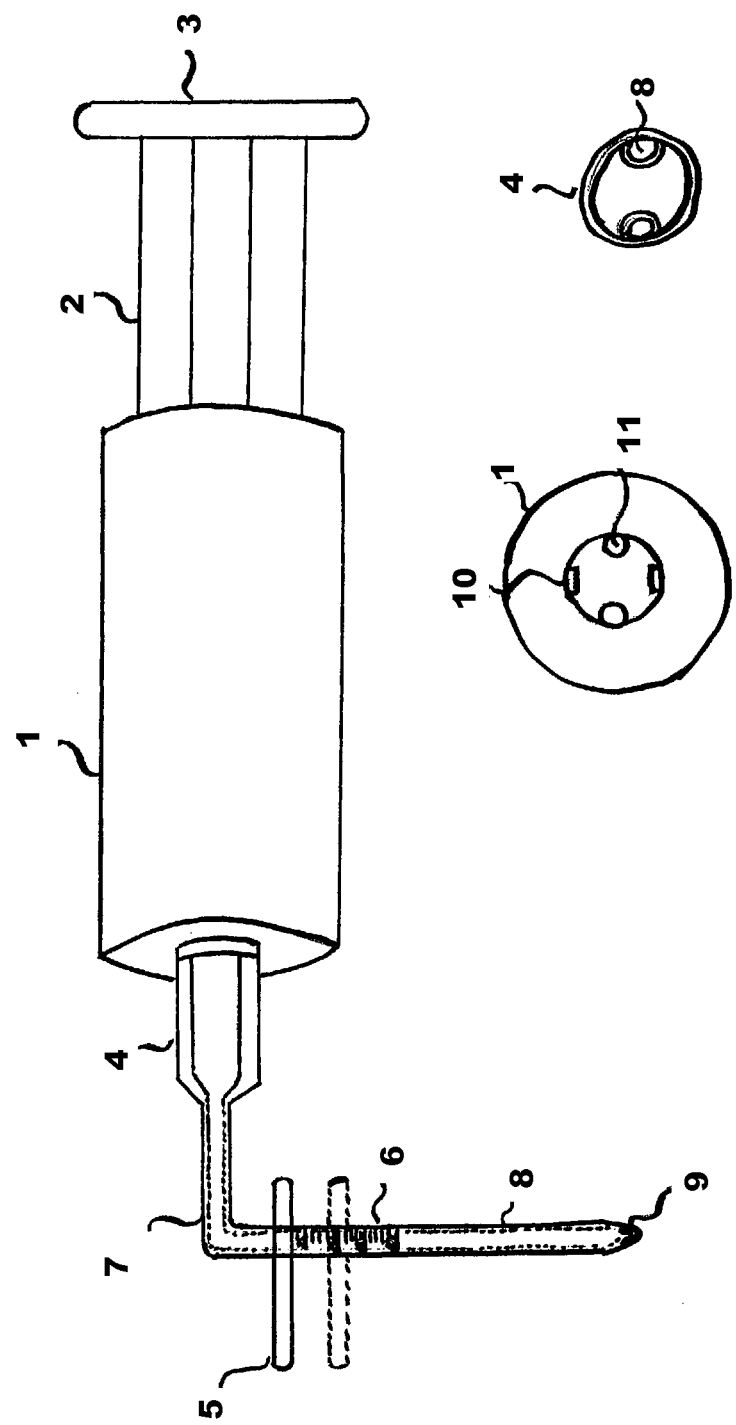

USE OF BONE ADHESIVE FOR APICAL SEALING A TOOTH ROOT CANAL

CROSS-REFERENCE TO RELATED APPLICATIONS

This application is a divisional application of U.S. application Ser. No. 12/094,845, which is the U.S. National Stage Entry of International Application PCT/EP2006/011519, filed Nov. 24, 2006, designating the U.S., and which claims the benefit of U.S. Provisional Application No. 60/739,738, filed Nov. 25, 2005 and also claims priority to European Application No. 05090327.7, filed Nov. 25, 2005 and German Patent Application No. 102006012777.3, filed Mar. 17, 2006. All of these applications are incorporated herein by reference in their entirety.

FIELD OF THE INVENTION

The invention relates to a method and a kit for producing a obturating means for apical sealing of a tooth root canal, for improving root canal fillings; the invention also relates to the use of bone adhesives for obturating root canals.

BACKGROUND OF THE INVENTION

It is known that the pulp of teeth react to sufficiently strong irritations—e.g., caries, trauma, or preparatory measures—with inflammations. These and other reasons may make a root canal treatment necessary. Independently of which method is used for the later therapeutic or prophylactic root filling, it is first necessary to open the tooth, including the pulp, using mechanical (e.g., drills) and chemical means.

The known preparations of the root canal relate to the expansion, cleaning, and shaping of the root canal, in particular through a biomechanical preparation, which particularly comprises filing and flushing the root canal until it is essentially absolutely shaped and cleaned. The root is subsequently filled, it being the goal of the root filling to hermetically seal the entire canal system as permanently as possible, to prevent the penetration of microorganisms or liquids after the treatment.

Various techniques are available to those skilled in the art for the root filling. One known technique is, for example, so-called lateral condensation, in which a long gutta-percha point—which fills up the tooth canal—coated with sealer is introduced into the previously prepared canal. By spreading and the insertion of further gutta-percha points, the channel is filled nearly completely. The lateral condensation of the accessory points allows an increase in density of the gutta-percha filling in this case, which is only possible in a very time-consuming manner, however. A further problem arises if too much sealer is applied to the gutta-percha point syringe or if excess sealer is used in general, because in this case the danger of overstuffing arises. The excess sealer material then squeezes out at the end of the root and intercalates in the surrounding bone.

A further tooth filling method comprises the use of thermoplastic filling material (THERMAFILL material, Dentsply Maillefer, Ballaigues, Switzerland). For the thermoplastic filling material it is necessary for a conically prepared channel to be available in the tooth, and for an intact apical terminus of the tooth to be provided—for example, by the introduction of sealer. However, these requirements for the thermoplastic filling material also simultaneously describe the decisive disadvantage of this method, because sealer may easily be pressed out beyond the apex. In this way, the cement material is pressed into the tissue surrounding the tooth and permanently intercalated. Undesired rejection reactions in the tissue or cyst formation may occur due to the intercalated cement material.

A further known method is thermoplastic condensation. The requirement for this is an intact and narrow apical foramen. In this method, a specially adapted gutta-percha point is plasticized by friction heat on the canal wall. The gutta-percha is rubbed apically and on the canal wall. The danger of overfilling with sealer also exists in this method.

In addition, those skilled in the art have the option of treating the root canal by a thermoplastic injection, in which gutta-percha heated outside the mouth is introduced into the canal using an injection syringe. Because the gutta-percha is introduced in the liquid state, the danger of overstuffing also exists here, by which gutta-percha material is introduced into the surrounding tissue beyond the tooth canal. A further disadvantage of this method is that an intact apical foramen must always be available as a requirement for a successful root filling.

All known methods share the feature that the filling material used may be pressed out of the root canal into the surrounding tissue due to the danger of overstuffing. In this way, inflammations and/or cyst formation may be initiated, which result in bone substance loss and significant pain for the patient. Moreover, a further main problem is the oval (at least nonround) shape of the apical foramen. Leaks thus arise in a filling system which has a round shape. Once these disadvantages have occurred, a revision of the entire method is necessary, and/or a root tip resection and/or the extraction of the tooth. Treatments of this type are connected with high costs and/or operative interventions.

BRIEF DESCRIPTION OF THE FIGURE

FIG. 1 is a schematic view of a device for apical introduction of a bone adhesive according to an exemplary embodiment of the invention.

DESCRIPTION OF VARIOUS AND PREFERRED EMBODIMENTS OF THE INVENTION

Object of the invention is therefore to provide means and methods which do not have the disadvantages of the prior art, and which in particular allow a simple, safe, and effective treatment of a tooth, in particular a safe and less time-consuming root filling, preferably a blockage which is free of tension peaks.

The invention achieves this object by the use of a bone adhesive for the apical blockage of a root canal.

The invention thus comprises apical root filling material, which preferably comprises or consists of physiological adhesive, such as bone adhesive or tissue adhesive. When a bone adhesive is cited in the meaning of the invention, this always also refers to tissue adhesive and thus all physiological adhesives. A root canal may be apically blocked using the invention, even if the canal has an oval or nonround shape at its apex, to preferably ensure a 100% seal in the area of the apex, or preferably if the circum-radicular bones (located around the root tip) display a bone substance loss. The bone adhesive used may comprise silicates and/or silanes, for example.

Preferred physiological adhesives or bone adhesives are calcium phosphate cements or their granules (for example, from the BAXTER company), but also monomers and comonomers, hydroxy apatite, polymers based on methyl acrylate and based on composites; furthermore, CERA-SORB adhesive (an adhesive which comprises calcium ions) may be used; further bone adhesives in the meaning of the invention are methacrylate, bone adhesive based on cement, and GELRIN adhesive (an adhesive comprising fibrin and glycol).

Further bone adhesives are known to those skilled in the art, such as fibrin adhesive.

Of course, it is possible to use the bone adhesive combined with a probe which comprises a gutta-percha stopper, for example.

The goal and subject of the teaching according to the invention is the obturation of the apical area of the open root canal, so that material introduced later which is used for the tooth filling may no longer enter the surrounding tissue by being pressed out of the root canal and may be used even with nonround apices and/or even with damaged circum-radicular bones. I.e., the use of the bone adhesive according to the invention is employed not only to completely fill up the root canal, but rather preferably for apical blockage. The blockage circumscribes the positioning of the bone adhesive in the apical area, so that subsequently introduced root filling material may not exit out of the root canal in the apical direction. The blockage hereby produced is preferably produced hermetical and/or bacteria-tight or essentially hermetical and/or essentially bacteria-tight. The method according to the invention according to the claims is performed both therapeutically and cosmetically. The method according to the invention is preferably not only used in the EPT member states for treating the human or animal body in the meaning that it has the goal of maintaining or restoring health or avoiding pain or discomfort. Accordingly, cosmetic problems, and/or problems which have an interfering influence on the dental health (but not harmful to health) are to be solved in particular by the method according to the invention in EPT member states. When reference is made in connection with the invention to therapeutic treatments or methods, it is therefore restricted in regard to EPT member states to the use of the means according to the invention for producing a treatment agent for the therapeutic treatment of pathological changes of the tooth root, in particular to the blockage and/or securing of the circum-radicular bones (located around the root tip) and securing the apical foramen. Therefore, the method may also be aimed at the production of a treatment agent which is used to restore a healthy state of a tooth root and/or to secure the apical foramen and/or to secure the periapical bone, when a bone adhesive is being used. If the teaching according to the invention, i.e., the method in this context, is also used in the USA and/or in a country in which no patent law based restrictions are provided in regard to treatment methods, the above-mentioned applications do not apply, so that the method is oriented directly to the therapeutic treatment of a tooth root canal.

The invention also relates to a tooth root sealing kit, which comprises at least one bone adhesive, possibly having information on combining or using the contents of the kit. Of course, it may also be possible that, in addition to the bone adhesive, the kit comprises probes which are used for sealing the root canal. For this purpose, it is preferable for the kit to comprise gutta-percha stoppers and/or various probes which have gutta-percha stoppers having various conicities. The information on combining the contents and using the contents of the kit, respectively, may comprise e.g., a treatment plan and a plan for treating or avoiding tooth lesions, respectively, in particular for treating root canals and filling them.

A method for root canal filling which is distinguished in that it comprises a subsequent root filling using the single-point technique, lateral condensation, and/or using thermoplastic filling material, is preferred.

An apical root filling material comprising bone adhesive and/or a gutta-percha stopper is preferred.

A root filling material is preferred, which is distinguished in that it does not extend into the non-apical area of the root canal and especially preferably covers ⅓ to ½ of the root canal length. Particularly preferably, ⅕ to 1/10 of the root canal length is covered, in particular not more than 1/10 of the total root length.

A method for the bacteria-tight obturation of a root canal, which is distinguished in that a separate apical obturation stopper is introduced into the root canal, the stopper comprising a bone adhesive, is preferred.

It is especially preferred if the bone adhesive and the tissue adhesive, respectively, is introduced into the root canal in such a manner that it overstuffs. The overstuffing is especially advantageous if it is performed in such a manner that the adhesive is pressed out of the root canal and penetrates into the surrounding tissue. Especially with lesions in the bone, more rapid healing and thus earlier conclusive care of the tooth may thus be performed.

The bone adhesive is preferably used for secure sealing with nonround foramina having lateral side channels; apical delta.

The adhesive, preferably bone adhesive, may especially preferably be used to apically obturate baby teeth, the bone adhesive being advantageous relative to the calcium hydroxide used until now (in particular for baby teeth).

In a preferred embodiment, the adhesive is to be synthesized in such a manner that it comprises components which allow both rapid fixation as well as slow fixation; such components are known to those skilled in the art. The slow bonding of the adhesive advantageously has the result that it penetrates into the tissue beyond the apex. The adhesive may also comprise materials which result in x-ray opacity. In addition, in a further preferred embodiment, the adhesive may also be admixed with bioresorbable granules.

Five different types of synthetic bone adhesives or cements are primarily advantageous: cyanoacrylates, polyurethanes, polymethylmethacrylates, epoxide resins, fibrin adhesives. These are preferably used above all for anchoring prostheses or for fixing small bone defects.

The cyanoacrylates were developed in 1959 by Coover et al. Various derivatives have been produced on this basis. The simplest is methyl-2-cyanoacrylate. Further derivatives have more carbon atoms, such as ethyl, butyl, and isobutyl 2-cyanoacrylate. The liquid monomers polymerize to form a solid polymer when water is added. They have a strong adhesive force above all even in a damp environment. Their adhesive force decreases with increasing number of carbon atoms, whereby elasticity and polymerization time increasing. However, the toxicity which is often observed also decreases with longer side chains. It is assumed that this toxicity originates above all from the degradation products. The cyanoacrylate adhesive has the great advantage of being able to be degraded. The adhesive is also used above all in gluing soft tissue parts.

Ostamer is the most well-known and best studied polyurethane; it polymerizes while forming cavities, so that bones may grow into these cavities. The polymerized polyurethane is preferably used as a framework material for the ingrowing bone.

Polymethylmethacrylate (PMMA) may be used as a bone cement, which may be a bone adhesive in the meaning of the invention. In particular, it may be used as a stabilizer and space filler of osteoporotic and tumorous bones in the tooth area. PMMA does not display any toxicity. PMMA meshes with the trabecular bones. In addition, PMMA is usable as a medication carrier, above all for antibiotics.

Epoxide resins are also advantageous as bone adhesives. Most fibrin adhesives are mixtures of fibrinogen, thrombin, calcium, and factor XIII. They represent the most physiological adhesive and therefore also do not display any allergic or toxic reactions. Further advantages also result therefrom. They are degraded within a short time without tissue irritation, this time possibly being too short for osseous consolidation. Furthermore, they do not display high polymerization temperatures. In addition, there are studies which describe an acceleration of the healing, hemostasis, and improved revascularization.

The invention also relates to a device for the apical introduction of bone adhesive into a root channel, the device comprising the following components: an adhesive depot, a pressure plunger, a pressure plunger top part, a standardized click attachment of a guide point, a rubber stopper for longitudinal securing, a measurement scale, a guide point having application tubes, an integrated application tube, an ISO-standardized point tip having laterally located application tube outlet ducts, a click system on the adhesive depot, and/or an application tube attachment.

The components of this device are preferably implemented in the injection molding method and are preferably to be produced from polymers.

The device accordingly comprises a dosing apparatus filled with two-component adhesive or a single-component adhesive, an attachment part having a mixing device, and a filling tube having a scale. Furthermore, it is also possible to use a cartridge having a dosing device in addition to the classical syringe version. The adhesive is hereby contained in a deformable cartridge which may be clamped in a reusable dosing device.

The invention also relates to a method for producing the mixing device, which has a cannula, it advantageously being implemented as a disposable article as an injection-moldable polymer.

TRICOS resorbable bone replacement material may preferably also be used as a bone adhesive. This is a resorbable, bioactive bone replacement material which may be especially preferably replaced by newly forming bony tissue. It comprises a two-phase ceramic made of calcium phosphate and beta-tri calcium phosphate.

The teaching according to the invention therefore has the following advantages:

turning away from standard technical practices
novel object
presence of a long unsolved urgent need for solving the problem solved by the invention
futile efforts of those skilled in the art until now
the simplicity of the solution speaks for inventive step, in particular because it replaces more complicated teaching
development of the scientific technology goes in another direction
development-tightening performance
false perceptions of those skilled in the art about the solution of the corresponding problem (prejudice)
technical progress, such as: improvement, performance increase, reduction in cost, savings in time, material, work steps, costs, or raw materials which are difficult to acquire, increased reliability, removal of errors, quality increase, freedom from maintenance, greater effectiveness, higher yield, increase of the technical possibilities, providing further means, opening a second pathway, opening a new field, first achievement of an object, reserve means, alternatives, possibilities for streamlining, automation, or miniaturization, or enrichment of the pharmaceutical storehouse
good selection, because a specific one was selected from a plurality of possibilities, whose result could not be predicted
error in citations
young field of the technology
combination invention, i.e., multiple known elements are compiled into a combination which has a surprising effect
licensing
commendation of the professional world and
economic success.

The above-mentioned advantages of the teaching according to the invention may be represented in detail as follows.

turning away from technical standard practices:
An apical stopper (located at the root tip) is introduced into the root canal (referred to in the following as RC), which is novel up to this point and has surprising results. A scaled, flexible application point following the curvature of the RC having integrated application tube or tubes is technically novel and is not obvious from the prior art.

novel object:
The main sources of error of unsuccessful RC, the overpressing of filler material and the leaks with nonround apices, are addressed and understood as the central object of using the bone adhesive. In addition, the filler material is even to be overstuffed to accelerate the healing of the bone. All other RC methods known until now are restricted to filling the canal per se, without placing special attention on the overstuffing of filler material and the leaks in the area of the apex.

fulfilling a need:
Overstuffing/overpressing and the leaks in the apical area and remedying them, which is an unmet need in nearly all RC methods, is met by the "adhesive".

futile efforts of those skilled in the art:
The methods of RC up to this point have only addressed the problems of overstuffing and the apical leaks indirectly, thus, for example, attempts have been made to find an apical obturation via friction heat and the plasticization of the gutta-percha resulting therefrom, which is unreliable and still contains the error source of overpressing and the apical leaks.

simplicity of the device:
A two-depot system having flexible, scaled cannula is to be triggered by a simple pressure mechanism. Complicated introduction of other filling material is dispensed with. The attached scale allows simple checking of the length at any time of the treatment.

improvement:
An apical stopper is introduced, for example, during the thermoplastic injection, which provides the improvements cited above and below. The danger of overpressing is minimized, nearly extinguished, and the consequences resulting therefrom such as inflammations, cyst formation, bone substance loss, and pain for the patient are also reduced to zero. In addition, the apical leaks are nearly extinguished and their consequences such as bacterial invasions of apices and destruction of the tooth enamel substance resulting therefrom are minimized. The "adhesive" is applicable with nearly all common methods. The "adhesive" is applicable even in the event of anatomical deviations, which represents a difference from the methods known up to this point.

reduction in cost:
The RC methods are improved (see above) and the treatment of an unsuccessful RC and/or overpressing, which is connected with enormous costs, is precluded. Costs in the event of a revision (removal of the old RC with subsequent new RC) are approximately € 800- € 1000; in America, the costs per canal are to be estimated at $1000 US, so that a complete tooth which may comprise four to five canals may cost up to $5,000 US. Costs for tooth extraction and subsequent care by implants, for example, run to approximately € 2000 per implant, etc.

protection of the patient:
The treatment of the points cited under "improvement" such as inflammation, cyst formation, and bone loss represent operative interventions. These not only cause further costs (e.g., bone construction in the event of bone loss), but also represent extreme psychic strains for the patient, inter alia, loss of self-esteem due to missing front teeth and exclusion from social society resulting therefrom, etc.

savings in time:
Difficult, cumbersome measurement of the typical guttapercha points is dispensed with by scaled measuring handle. An x-ray picture (Masterpoint) is dispensed with. This is not only a savings in time, but rather also a lesser strain of the patient by x-rays. Furthermore, this savings also represents a cost savings (x-ray machine, x-ray images, personnel, etc.). General savings in work time due to simple handling.

reliability:
Provided by simple handling and liquid decanting of the material, all lateral openings in the apical area are obturated without having to worry about the overstuffing of material. Scaling on the measurement handle makes the work more precise and reliable.

freedom from maintenance:
Provided by disposable system of the adhesive cannula.

greater effectiveness:
Results from combination of the above-mentioned points, such as simplicity, reliability, freedom from maintenance, etc.

combination invention:
Known RC materials such as the bone adhesive are unified and combined with the newly developed measurement handle.

economic success:
Economic success is to be expected through cost-effective provision of the products and their simple handling including the improvement of the typical techniques.

The invention is explained in greater detail hereafter on the basis of examples and drawings, without being restricted thereto.

EXAMPLES

The plastic of the preferred instrument according to the invention is selected in such a manner that it is biocompatible, flexible and elastic, resistant to compression, non-toxic, and resilient. It is produced in such a manner that the instrument (application cannula) are to be used as a disposable system. Furthermore, the scale of the instrument is kept in 0.5 mm steps, every whole 1 mm step being shown by full circles and every 0.5 mm step being shown by half circles. A different color is selected for the scale every 5 mm, so that the person performing treatment may perform the length check at any time. In addition, the length is imprinted in the form of a number on every fifth partial stroke (for example: a 20 stands next to the scale stroke at the length 20 mm).

FIG. 1:
FIG. 1 shows a device for apical introduction of a bone adhesive into a root canal of a tooth according to an exemplary embodiment of the invention. The device includes an adhesive depot 1, a pressure plunger 2, a pressure plunger top part 3, a standardized click attachment 4 for a guide cannula 7, a movable rubber stopper 5 for longitudinal securing the guide cannula 7, a measurement scale 6, the guide cannula 7 having a plurality of application tubes 8 (or only one application tube) integrated therein, the guide cannula 7 having an ISO-standardized point tip having laterally located application tubie outlet ducts 9. The adhesive depot 1 includes a click system 10 and a reinforced application tube attachment 11.

The two main components (or only one component) of the bone adhesive are stored in (one or) two separate depots 1 in the handle part of the syringe. As a result, the injection cannula can also be used as a disposable system. The same plastic is used for the guide cannula and for a probe (not shown) according to an exemplary embodiment of the invention. Injection tubes are located on the left side and on the right side (or only one injection tube is centrally located) in the guide cannula to convey the components of the bone adhesive in an apical direction (toward the root tip) so that the two components flow together there. The scale is designed in the same way as explained above for FIG. 1.

What I claim is:
1. A method for apically blocking a root canal, the method comprising:
preparing an open root canal of a tooth for a root canal treatment;
providing a bone adhesive;
said bone adhesive being made of epoxide resin, cyanoacrylates, polyurethanes, polymethylmethacrylates or a fibrin adhesive;
said bone adhesive being bioresorbable and/or admixed with bioresorbable granules;
providing a root canal filling material;
said root canal filling material being susceptible to cause inflammations as it is intercalated in surrounding tissue of the tooth;
preventing inflammations, cyst formation and loss of substance of a circum-radicular bone and accelerating healing of the circum-radicular bone when the circum-radicular bone displays a bone substance loss by:
introducing into the open root canal said bone adhesive with a probe having a ore-determined conicity so as to apically block the root canal, overstuff the root canal and press the bone adhesive out of an apical foramen of the root canal with the probe;
controlling an amount of said bone adhesive introduced into the open root canal so as to prevent said bone adhesive to extend into non-apical areas of the root canal and to cover not more than ⅓ of a root canal length; and
subsequently introducing into the open root canal the root canal filling material so as to prevent the root canal filling material from being overstuffed and pressed out of the root canal.
2. The method of claim 1, wherein the root canal has a nonround apex and/or damaged circum radicular bones.

3. The method of claim 2, wherein the root canal has a nonround foramen having lateral side channels.

4. The method of claim 1, wherein an apical blockage produced by the bone adhesive is hermetical and/or bacteria tight.

5. The method of claim 1, wherein the bone adhesive covers ⅕ to 1/10 of the root canal length.

6. The method of claim 1, wherein the bone adhesive covers not more than 1/10 of the root canal length.

7. The method of claim 1, wherein the root canal filling material that is introduced into the open root canal subsequent to the bone adhesive does not enter the surrounding tissues.

8. The method of claim 7, wherein the root canal filling material does not exit out of the root canal in apical direction.

9. The method of claim 1, wherein the method is a therapeutic method and the bone adhesive is administered in an amount effective to treat pathological changes of the tooth root.

10. The method of claim 9, wherein a healthy state of the tooth root is restored.

11. The method of claim 9, wherein a circum radicular bone is blocked and/or secured and an apical foramen is secured.

12. The method of claim 1, wherein the root canal filling material is introduced into the open root canal subsequent to the bone adhesive utilizing a single point technique and lateral condensation.

13. The method of claim 12, wherein the root canal filling material is a thermoplastic filling material.

14. The method of claim 1, wherein the bone adhesive is resorbable and includes a two phase ceramic made of calcium phosphate and beta-tri calcium phosphate.

15. A method for apically blocking a root canal, the method comprising:
   preparing an open root canal of a tooth for a root canal treatment;
   providing a bone adhesive;
   said bone adhesive being made of epoxide resin, cyanoacrylates, polyurethanes, polymethylmethacrylates or a fibrin adhesive;
   said bone adhesive being bioresorbable and/or admixed with bioresorbable granules;
   providing a root canal filling material;
   said root canal filling material being made of a thermoplastic filling material and/or a cement material;
   said root canal filling material being susceptible to cause inflammations as it is intercalated into surrounding tissue of the tooth;
   preventing the root canal filling material from intercalating in the surrounding tissue of the tooth to prevent inflammations, cyst formation and loss of substance of a circum-radicular bone and to accelerate healing of the circum-radicular bone when the circum-radicular bone displays a bone substance loss by:
      introducing into the open root canal said bone adhesive with a probe having a re-determined conicity so as to apically block the root canal;
      overstuff the root canal and press the bone adhesive out of lateral side channels of an apical foramen of the root canal with the probe;
      allowing penetration of said bone adhesive into the surrounding tissue;
      controlling an amount of said bone adhesive introduced into the open root canal so as to prevent said bone adhesive from extending into non-apical areas of the root canal and to cover not more than ⅓ of a root canal length; and,
      subsequently introducing into the open root canal the root canal filling material so as to prevent the root canal filling material from being overstuffed and pressed out of the root canal.

16. The method of claim 15, wherein the root canal filling material is introduced into the open root canal subsequent to the bone adhesive utilizing a single point technique and lateral condensation.

17. The method of claim 15, wherein the root canal filling material is introduced into the open root canal subsequent to the bone adhesive utilizing a thermoplastic injection technique.

18. The method of claim 1, wherein said root canal filling material is made of a thermoplastic filling material.

19. The method of claim 1, wherein said root canal filling material is made of a cement material.

* * * * *

UNITED STATES PATENT AND TRADEMARK OFFICE
CERTIFICATE OF CORRECTION

PATENT NO. : 9,724,173 B2  
APPLICATION NO. : 14/043976  
DATED : August 8, 2017  
INVENTOR(S) : Markus Lietzau It is certified that error appears in the above-identified patent and that said Letters Patent is hereby corrected as shown below:

In the Claims

Column 8, Line 53, Claim 1 change "ore-determined" to -- pre-determined --.

Column 10, Line 14, Claim 15 change "re-determined" to -- pre-determined --.

Signed and Sealed this  
Twenty-fourth Day of October, 2017

Joseph Matal  
*Performing the Functions and Duties of the*  
*Under Secretary of Commerce for Intellectual Property and*  
*Director of the United States Patent and Trademark Office*